(12) United States Patent
Gross

(10) Patent No.: US 11,357,629 B1
(45) Date of Patent: Jun. 14, 2022

(54) DIASTOLIC HEART FAILURE TREATMENT

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 0 days.

(21) Appl. No.: 17/509,727

(22) Filed: Oct. 25, 2021

(51) Int. Cl.
*A61F 2/24* (2006.01)

(52) U.S. Cl.
CPC .......... *A61F 2/2445* (2013.01); *A61F 2/2466* (2013.01)

(58) Field of Classification Search
CPC ........ A61F 2/24; A61F 2/2445; A61F 2/2466; A61F 2220/0016; A61F 2220/0075; A61F 2/2481; A61B 17/04–0493; A61B 2017/0403–0498
See application file for complete search history.

(56) References Cited

U.S. PATENT DOCUMENTS

| | | |
|---|---|---|
| 4,546,759 A | 10/1985 | Solar |
| 4,994,017 A | 2/1991 | Yozu |
| 4,994,078 A | 2/1991 | Jarvik |
| 5,139,517 A | 8/1992 | Corral |
| 5,762,599 A | 6/1998 | Sohn |
| 5,810,757 A | 9/1998 | Sweezer, Jr. et al. |
| 5,891,012 A | 4/1999 | Downey et al. |
| 6,332,893 B1 | 12/2001 | Mortier et al. |
| 6,406,422 B1 | 6/2002 | Landesberg |
| 6,432,039 B1 | 8/2002 | Wardle |
| 7,159,593 B2 | 1/2007 | McCarthy et al. |
| 7,404,824 B1 | 7/2008 | Webler et al. |
| 7,431,692 B2 | 10/2008 | Zollinger et al. |
| 7,476,200 B2 | 1/2009 | Tal |
| 7,483,743 B2 | 1/2009 | Mann et al. |
| 7,635,329 B2 | 12/2009 | Goldfarb et al. |
| 7,862,501 B2 | 1/2011 | Woodard |

(Continued)

FOREIGN PATENT DOCUMENTS

| | | |
|---|---|---|
| WO | 2004/066805 | 8/2004 |
| WO | 2004/108191 | 12/2004 |

(Continued)

OTHER PUBLICATIONS

Carlsson M et al., "Atrioventricular plane displacement is the major contributor to left ventricular pumping in healthy adults, athletes, and patients with dilated cardiomyopathy," Am J Physiol Heart Circ Physiol 292: H1452-H1459, 2007.

*Primary Examiner* — Brian A Dukert
*Assistant Examiner* — Rebecca Lynee Zimmerman
(74) *Attorney, Agent, or Firm* — Sughrue Mion, PLLC

(57) ABSTRACT

A method of treating diastolic heart failure includes implanting a cardiac implant in a heart of a subject diagnosed as suffering from diastolic heart failure. A superior portion of a flexible tether of the cardiac implant is anchored to one or more left-atrial sites of one or more walls of the left atrium. An inferior portion of the flexible tether is anchored to a site of a wall of a mid third of the left ventricle, of a wall of an apical third of the left ventricle, and/or of a papillary muscle of the left ventricle. As a result, the flexible tether reduces a volume of the left atrium during at least a portion of ventricular diastole of each cardiac cycle, thereby enhancing ventricular filling. Other embodiments are also described.

31 Claims, 7 Drawing Sheets

(56) References Cited

U.S. PATENT DOCUMENTS

| | | |
|---|---|---|
| 7,927,268 B1 | 4/2011 | St. Germain et al. |
| 8,057,493 B2 | 11/2011 | Goldfarb et al. |
| 8,147,542 B2 | 4/2012 | Maisano et al. |
| 8,475,525 B2 | 7/2013 | Maisano et al. |
| 8,591,576 B2 * | 11/2013 | Hasenkam ............ A61F 2/2466 623/2.37 |
| 8,790,394 B2 | 7/2014 | Miller et al. |
| 8,876,850 B1 | 11/2014 | Vollmers et al. |
| 8,961,596 B2 | 2/2015 | Maisano et al. |
| 9,232,999 B2 | 1/2016 | Maurer et al. |
| 9,517,129 B2 | 12/2016 | Wilson et al. |
| 9,545,305 B2 | 1/2017 | Wilson et al. |
| 9,833,316 B2 | 12/2017 | Wilson et al. |
| 10,039,643 B2 | 8/2018 | Gilmore et al. |
| 10,039,874 B2 | 8/2018 | Schwammenthal et al. |
| 10,098,992 B2 | 10/2018 | Van Dort et al. |
| 10,286,131 B2 | 5/2019 | Sohn et al. |
| 10,405,978 B2 | 9/2019 | Maisano et al. |
| 10,517,719 B2 | 12/2019 | Miller et al. |
| 10,610,360 B2 | 4/2020 | Reich et al. |
| 10,722,631 B2 | 7/2020 | Salahieh et al. |
| 10,751,184 B2 | 8/2020 | Reich et al. |
| 10,820,998 B2 | 11/2020 | Marr et al. |
| 10,888,644 B2 | 1/2021 | Ratz et al. |
| 10,973,966 B2 | 4/2021 | Sohn et al. |
| 11,051,940 B2 | 7/2021 | Metchik et al. |
| 2002/0169360 A1 | 11/2002 | Taylor et al. |
| 2002/0173742 A1 | 11/2002 | Keren et al. |
| 2003/0216801 A1 | 11/2003 | Tweden et al. |
| 2004/0111006 A1 | 6/2004 | Alferness et al. |
| 2005/0148925 A1 | 7/2005 | Rottenberg et al. |
| 2005/0154250 A1 | 7/2005 | Aboul-hosn et al. |
| 2005/0165344 A1 | 7/2005 | Dobak, III |
| 2005/0256566 A1 | 11/2005 | Gabbay |
| 2006/0064059 A1 | 3/2006 | Gelfand et al. |
| 2006/0206029 A1 | 9/2006 | Yair |
| 2006/0241745 A1 | 10/2006 | Solem |
| 2007/0073218 A1 | 3/2007 | Lau et al. |
| 2007/0299296 A1 | 12/2007 | Vaska |
| 2008/0004485 A1 | 1/2008 | Moreschi |
| 2008/0207986 A1 | 8/2008 | Choy |
| 2010/0023117 A1 | 1/2010 | Yoganathan et al. |
| 2010/0057192 A1 | 3/2010 | Celermajer |
| 2010/0298929 A1 | 11/2010 | Thornton et al. |
| 2011/0112632 A1 | 5/2011 | Chau et al. |
| 2011/0218480 A1 | 9/2011 | Rottenberg et al. |
| 2011/0306916 A1 | 12/2011 | Nitzan et al. |
| 2012/0059213 A1 | 3/2012 | Spence |
| 2012/0143320 A1 | 6/2012 | Eliasen et al. |
| 2014/0213959 A1 | 7/2014 | Nitzan et al. |
| 2015/0335801 A1 | 11/2015 | Farnan et al. |
| 2016/0015877 A1 | 1/2016 | Guerrero et al. |
| 2016/0166747 A1 | 6/2016 | Frazier et al. |
| 2017/0136162 A1 | 5/2017 | Van Dort et al. |
| 2017/0231766 A1 | 8/2017 | Hariton et al. |
| 2017/0325949 A1 | 11/2017 | Rodgers et al. |
| 2018/0001004 A1 | 1/2018 | Sohn et al. |
| 2020/0188101 A1 | 6/2020 | Chambers |
| 2021/0022858 A1 | 1/2021 | Miller et al. |
| 2021/0121679 A1 | 4/2021 | Mohl et al. |

FOREIGN PATENT DOCUMENTS

| | | |
|---|---|---|
| WO | 2007/132449 | 11/2007 |
| WO | 2007/149562 | 12/2007 |
| WO | 2008/141325 A1 | 11/2008 |
| WO | 2010/128501 | 11/2010 |
| WO | 2014/203078 | 12/2014 |
| WO | 2015/177793 | 11/2015 |
| WO | 2016/113743 | 7/2016 |
| WO | 2020/081481 | 4/2020 |

* cited by examiner

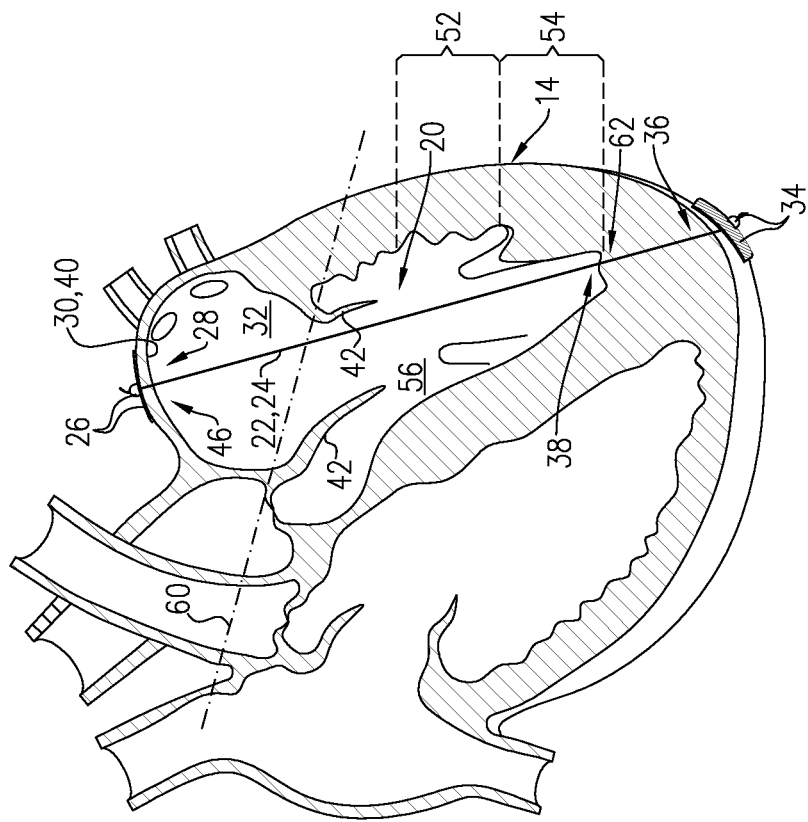
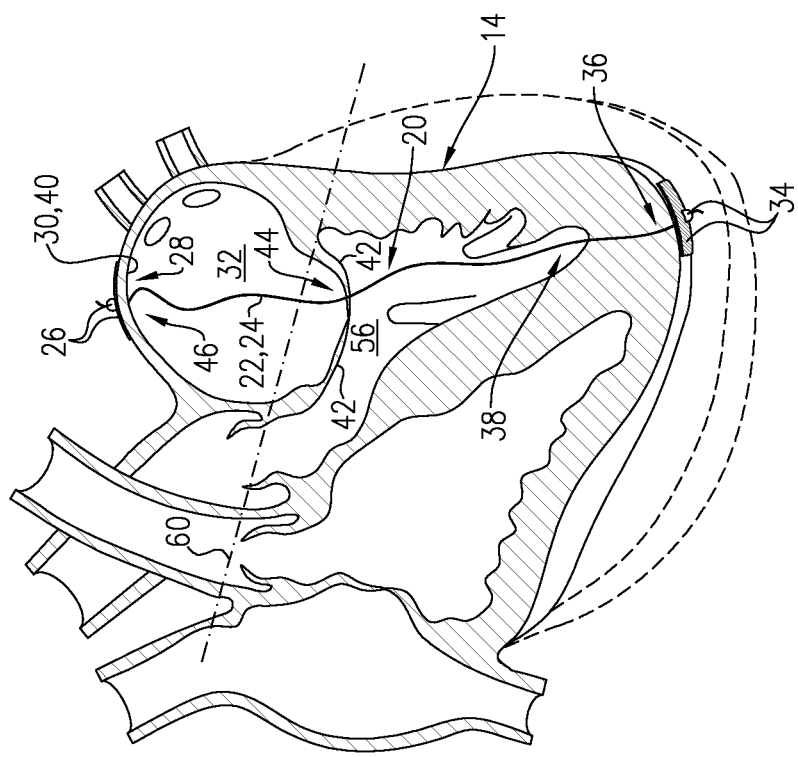
FIG. 1A
FIG. 1B

DIASTOLIC HEART FAILURE TREATMENT

FIELD OF THE APPLICATION

The present invention relates generally to techniques for treatment of heart failure, and specifically to minimally-invasive techniques for mechanical treatment of diastolic heart failure.

BACKGROUND OF THE APPLICATION

In diastolic heart failure, the left ventricle does not fill properly with blood during diastole, reducing the amount of blood pumped to the body. Diastolic is also known as heart failure with preserved ejection fraction (HFpEF). Diastolic heart failure may or may not be accompanied by mitral regurgitation.

SUMMARY OF THE APPLICATION

Some embodiments of the present invention provide a cardiac implant and a method for treating diastolic heart failure. The cardiac implant is typically implanted in a subject diagnosed as suffering from diastolic heart failure, with or without mitral regurgitation. The cardiac implant comprises an elongate member, a superior anchor, and an inferior anchor. The superior anchor is coupled to a superior portion of the elongate member and configured to anchor the elongate member to one or more left-atrial sites of one or more walls of a left atrium of a heart. The inferior anchor is coupled to an inferior portion of the elongate member and configured to anchor the elongate member to one or more left-ventricular sites of a left ventricle of the heart.

The cardiac implant is implanted by anchoring the superior portion of the elongate member to the one or more left-atrial sites, and the inferior portion of the elongate member to the one or more of the left-ventricular sites, such that the elongate member reduces a volume of the left atrium during at least a portion of ventricular diastole of each cardiac cycle, thereby enhancing ventricular filling. The reduction in the volume of the left atrium increases pressure in the left atrium and thus the volume of blood flow from the left atrium to the left ventricle. The cardiac implant is automatically synchronized with the cardiac cycle.

For some applications, the elongate member reduces the volume of the left atrium by approximating (i.e., moving closer together) a left atrial roof and a left atrioventricular (AV) plane during the at least a portion of ventricular diastole of each cardiac cycle. Typically, to do so, during the at least a portion of ventricular diastole, the elongate member holds the left atrial roof at a fixed distance from a ventricular apex. As the left AV plane and the ventricular apex move away from each other during the rapid filling phase of diastole, the elongate member prevents the left atrial roof and the ventricular apex from also moving away from each other. As a result, the left atrial roof and the left AV plane are approximated. The elongate member thus reduces the volume of the left atrium beginning during the rapid filling phase of diastole of each cardiac cycle, thereby enhancing ventricular filling from the left atrium during diastole.

Typically, the superior and the inferior portions of the elongate member are anchored such that the elongate member does not interfere with leaflets of a mitral valve.

For some applications, the elongate member comprises a flexible tether, while for other applications, the elongate member comprises a rod.

For some applications in which the elongate member comprises the flexible tether, the superior and the inferior portions of the flexible tether are anchored such that the flexible tether is slack during ventricular systole and taut at least during the portion of ventricular diastole during which the flexible tether reduces the volume of the left atrium. The slackness of the flexible tether during ventricular systole helps prevent any possible interference by the flexible tether with coaptation of the leaflets of the mitral valve during systole. The tautness of the flexible tether during the portion of ventricular diastole does not interfere with the mitral valve, because the leaflets are open during diastole in any event.

There is therefore provided, in accordance with an Inventive Concept 1 of the present invention, a method of treating diastolic heart failure, including implanting a cardiac implant in a heart of a subject diagnosed as suffering from diastolic heart failure, wherein implanting includes:

anchoring a superior portion of a flexible tether of the cardiac implant to one or more left-atrial sites of one or more walls of a left atrium of the heart; and anchoring an inferior portion of the flexible tether to one or more left-ventricular sites of a left ventricle of the heart selected from the group of sites consisting of: (a) a site of a wall of a mid third of the left ventricle, (b) a site of a wall of an apical third of the left ventricle, and (c) a site of a papillary muscle of the left ventricle, such that the flexible tether reduces a volume of the left atrium during at least a portion of ventricular diastole of each cardiac cycle, thereby enhancing ventricular filling.

Inventive Concept 2. The method according to Inventive Concept 1, wherein implanting the cardiac implant in the heart of the subject includes implanting the cardiac implant in the heart of a subject diagnosed as suffering from diastolic heart failure without mitral regurgitation.

Inventive Concept 3. The method according to Inventive Concept 1, wherein implanting the cardiac implant in the heart of the subject includes implanting the cardiac implant in the heart of a subject diagnosed as suffering from diastolic heart failure without severe mitral regurgitation.

Inventive Concept 4. The method according to Inventive Concept 1, wherein implanting the cardiac implant includes implanting the cardiac implant such that the cardiac implant does not provide a surface having an area of at least 1 cm2 against which leaflets of a mitral valve of the heart coapt during systole of each cardiac cycle.

Inventive Concept 5. The method according to Inventive Concept 1, wherein implanting the cardiac implant includes implanting the cardiac implant such that the cardiac implant does not impede motion of leaflets of a mitral valve of the heart during each cardiac cycle.

Inventive Concept 6. The method according to Inventive Concept 1, wherein implanting the cardiac implant includes implanting the cardiac implant such that the cardiac implant does not impede regurgitative blood flow through a mitral valve of the heart.

Inventive Concept 7. The method according to Inventive Concept 1, wherein implanting the cardiac implant includes implanting the cardiac implant so as to treat the diastolic heart failure without acutely treating mitral regurgitation.

Inventive Concept 8. The method according to Inventive Concept 1, wherein implanting the cardiac implant includes anchoring the superior and the inferior portions of the flexible tether such that the flexible tether reduces the volume of the left atrium by approximating a left atrial roof and a left atrioventricular (AV) plane during the at least a portion of ventricular diastole of each cardiac cycle.

Inventive Concept 9. The method according to Inventive Concept 1, wherein implanting the cardiac implant includes anchoring the superior and the inferior portions of the flexible tether such that the flexible tether reduces the volume of the left atrium beginning during a rapid filling phase of diastole of each cardiac cycle.

Inventive Concept 10. The method according to Inventive Concept 1, wherein implanting the cardiac implant includes anchoring the superior and the inferior portions of the flexible tether such that the flexible tether is slack during ventricular systole and taut at least during the portion of ventricular diastole during which the flexible tether reduces the volume of the left atrium.

Inventive Concept 11. The method according to Inventive Concept 1, wherein the flexible tether is non-extensible.

Inventive Concept 12. The method according to Inventive Concept 1, wherein implanting the cardiac implant includes anchoring the superior and the inferior portions of the flexible tether such that the flexible tether has a length of 6-12 cm between the one or more left-atrial sites and the one or more left-ventricular sites.

Inventive Concept 13. The method according to Inventive Concept 1, wherein the flexible tether is elastic.

Inventive Concept 14. The method according to Inventive Concept 1, further including adjusting a length of the flexible tether between the one or more left-atrial sites and the one or more left-ventricular sites after anchoring the superior and the inferior portions of the flexible tether.

Inventive Concept 15. The method according to Inventive Concept 14, wherein adjusting the length of the tether includes rotating a spool disposed along or at either end of the flexible tether.

Inventive Concept 16. The method according to Inventive Concept 14, wherein adjusting the length of the flexible tether includes:
  assessing one or more cardiac parameters during one or more pre-adjustment cardiac cycles; and
  adjusting the length of the flexible tether responsively to the one or more cardiac parameters.

Inventive Concept 17. The method according to Inventive Concept 16, wherein assessing the one or more cardiac parameters includes performing echocardiography.

Inventive Concept 18. The method according to Inventive Concept 14, wherein adjusting the length of the flexible tether includes:
  measuring left ventricular end-diastolic volume during one or more pre-adjustment cardiac cycles; and
  adjusting the length of the flexible tether so as to increase the left ventricular end-diastolic volume during one more post-adjustment cardiac cycles.

Inventive Concept 19. The method according to Inventive Concept 14, wherein adjusting the length of the flexible tether includes adjusting the length of the flexible tether such that the flexible tether is slack at least at an end of ventricular systole.

Inventive Concept 20. The method according to Inventive Concept 19, wherein adjusting the length of the flexible tether includes selecting a degree of slackness of the flexible tether in order to set a desired time of commencement of tautness of the flexible tether during diastole of each cardiac cycle.

Inventive Concept 21. The method according to Inventive Concept 19, wherein adjusting the length of the flexible tether includes selecting a degree of slackness of the flexible tether in order to set a desired maximum distance between the left atrial roof and a left atrioventricular plane during the at least a portion of ventricular diastole.

Inventive Concept 22. The method according to Inventive Concept 19, wherein adjusting the length of the flexible tether includes:
  assessing, at the end of ventricular systole of one or more cardiac cycles, a location of the left atrial roof with respect to the left AV plane; and
  responsively to the location, adjusting the length of the flexible tether such that the flexible tether is slack at least at the end of ventricular systole.

Inventive Concept 23. The method according to Inventive Concept 14, wherein adjusting the length of the flexible tether includes adjusting the length of the flexible tether during an implantation procedure in which the anchoring of the superior and the inferior portions of the flexible tether is performed.

Inventive Concept 24. The method according to Inventive Concept 14, wherein adjusting the length of the flexible tether includes adjusting the length of the flexible tether at least 24 hours after anchoring the superior and the inferior portions of the flexible tether.

Inventive Concept 25. The method according to Inventive Concept 1, wherein implanting the cardiac implant includes:
  measuring left ventricular end-diastolic volume during one or more cardiac cycles; and
  setting a length of the flexible tether between the one or more left-atrial sites and the one or more left-ventricular sites so as to increase the left ventricular end-diastolic volume during one or more subsequent cardiac cycles.

Inventive Concept 26. The method according to Inventive Concept 1, wherein implanting the cardiac implant includes setting a length of the flexible tether between the one or more left-atrial sites and the one or more left-ventricular sites such that the flexible tether is slack at least at an end of ventricular systole.

Inventive Concept 27. The method according to Inventive Concept 26, wherein setting the length of the flexible tether between the one or more left-atrial sites and the one or more left-ventricular sites includes selecting a degree of slackness of the flexible tether in order to set a desired time of commencement of tautness of the flexible tether during diastole of each cardiac cycle.

Inventive Concept 28. The method according to Inventive Concept 26, wherein setting the length of the flexible tether between the one or more left-atrial sites and the one or more left-ventricular sites includes selecting a degree of slackness of the flexible tether in order to set a desired maximum distance between the left atrial roof and a left atrioventricular plane during the at least a portion of ventricular diastole.

Inventive Concept 29. The method according to Inventive Concept 26, wherein setting the length of the flexible tether includes:
  assessing, at the end of ventricular systole of one or more cardiac cycles, a location of the left atrial roof with respect to the left AV plane; and
  responsively to the location, setting the length of the flexible tether between the one or more left-atrial sites 46 and the one or more left-ventricular sites 38 such that the flexible tether is slack at least at the end of ventricular systole.

Inventive Concept 30. The method according to Inventive Concept 1, wherein anchoring the superior portion of the flexible tether to the one or more left-atrial sites of the one or more left atrial walls includes anchoring the superior portion of the flexible tether to the left atrial roof.

Inventive Concept 31. The method according to Inventive Concept 1, wherein the superior portion of the flexible tether is bifurcated, and wherein anchoring the superior portion of the flexible tether to the one or more left-atrial sites of the one or more left atrial walls includes anchoring bifurcations of the superior portion of the flexible tether to two respective left-atrial sites of the one or more left atrial walls.

Inventive Concept 32. The method according to Inventive Concept 1, wherein anchoring the superior portion of the flexible tether includes anchoring the superior portion of the flexible tether to the one or more left-atrial sites of the one or more walls of the left atrium of the heart of a subject diagnosed as suffering from diastolic heart failure with mitral regurgitation.

Inventive Concept 33. The method according to Inventive Concept 32, further including positioning a mitral valve clip along the flexible tether and coupling the mitral valve clip to two or more leaflets of a mitral valve of the heart so as to coapt the two or more leaflets.

Inventive Concept 34. The method according to Inventive Concept 33, wherein positioning the mitral valve clip along the flexible tether includes positioning the mitral valve clip along the flexible tether such that the flexible tether passes through a central passage of the mitral valve clip.

Inventive Concept 35. The method according to Inventive Concept 32, wherein implanting the cardiac implant includes passing the flexible tether through an edge-to-edge stitch that approximates free edges of two or more leaflets of a mitral valve of the heart.

Inventive Concept 36. The method according to Inventive Concept 1, wherein implanting the cardiac implant includes passing the flexible tether through a centering ring coupled to a frame of a prosthetic mitral valve implanted at a mitral valve of the heart.

There is further provided, in accordance with an Inventive Concept 37 of the present invention, a method of treating diastolic heart failure, including implanting a cardiac implant in a heart of a subject diagnosed as suffering from diastolic heart failure, wherein implanting includes:

anchoring a superior portion of an elongate member of the cardiac implant to one or more left-atrial sites of one or more walls of a left atrium of the heart; and anchoring an inferior portion of the elongate member to one or more left-ventricular sites of a left ventricle of the heart selected from the group of sites consisting of: (a) a site of a wall of a mid third of the left ventricle, (b) a site of a wall of an apical third of the left ventricle, and (c) a site of a papillary muscle of the left ventricle, such that the elongate member reduces a volume of the left atrium during at least a portion of ventricular diastole of each cardiac cycle, thereby enhancing ventricular filling, and such that the cardiac implant does not provide a surface having an area of at least 1 cm2 against which leaflets of a mitral valve of the heart coapt during systole of each cardiac cycle.

Inventive Concept 38. The method according to Inventive Concept 37, wherein the elongate member is a rod, and wherein implanting the cardiac implant includes anchoring the superior and the inferior portions of the rod.

Inventive Concept 39. The method according to Inventive Concept 37, wherein the elongate member is a flexible tether, and wherein implanting the cardiac implant includes anchoring the superior and the inferior portions of the flexible tether.

Inventive Concept 40. The method according to Inventive Concept 37, wherein implanting the cardiac implant in the heart of the subject includes implanting the cardiac implant in the heart of a subject diagnosed as suffering from diastolic heart failure without mitral regurgitation.

Inventive Concept 41. The method according to Inventive Concept 37, wherein implanting the cardiac implant in the heart of the subject includes implanting the cardiac implant in the heart of a subject diagnosed as suffering from diastolic heart failure without severe mitral regurgitation.

Inventive Concept 42. The method according to Inventive Concept 37, wherein implanting the cardiac implant includes implanting the cardiac implant such that the cardiac implant does not impede motion of leaflets of a mitral valve of the heart during each cardiac cycle.

Inventive Concept 43. The method according to Inventive Concept 37, wherein implanting the cardiac implant includes implanting the cardiac implant such that the cardiac implant does not impede regurgitative blood flow through a mitral valve of the heart.

Inventive Concept 44. The method according to Inventive Concept 37, wherein implanting the cardiac implant includes implanting the cardiac implant so as to treat the diastolic heart failure without acutely treating mitral regurgitation.

Inventive Concept 45. The method according to Inventive Concept 37, wherein implanting the cardiac implant includes anchoring the superior and the inferior portions of the elongate member such that the elongate member reduces the volume of the left atrium by approximating a left atrial roof and a left atrioventricular (AV) plane during the at least a portion of ventricular diastole of each cardiac cycle.

Inventive Concept 46. The method according to Inventive Concept 37, wherein implanting the cardiac implant includes anchoring the superior and the inferior portions of the elongate member such that the elongate member reduces the volume of the left atrium beginning during a rapid filling phase of diastole of each cardiac cycle.

Inventive Concept 47. The method according to Inventive Concept 37, wherein the elongate member has a length of 6-12 cm between the one or more left-atrial sites and the one or more left-ventricular sites.

Inventive Concept 48. The method according to Inventive Concept 37, wherein implanting the cardiac implant includes:

measuring left ventricular end-diastolic volume during one or more cardiac cycles; and setting a length of the elongate member between the one or more left-atrial sites and the one or more left-ventricular sites so as to increase the left ventricular end-diastolic volume during one or more subsequent cardiac cycles.

Inventive Concept 49. The method according to Inventive Concept 37, wherein anchoring the superior portion of the elongate member to the one or more left-atrial sites of the one or more left atrial walls includes anchoring the superior portion of the elongate member to the left atrial roof.

Inventive Concept 50. The method according to Inventive Concept 37, wherein the superior portion of the elongate member is bifurcated, and wherein anchoring the superior portion of the elongate member to the one or more left-atrial sites of the one or more left atrial walls includes anchoring bifurcations of the superior portion of the elongate member to two respective left-atrial sites of the one or more left atrial walls.

Inventive Concept 51. The method according to Inventive Concept 37, wherein anchoring the superior portion of the elongate member includes anchoring the superior portion of the elongate member to the one or more left-atrial sites of the one or more walls of the left atrium of the heart of a subject diagnosed as suffering from diastolic heart failure with mitral regurgitation.

There is still further provided, in accordance with an Inventive Concept 52 of the present invention, includes cardiac implant for treating diastolic heart failure, the cardiac implant including:

a flexible tether;

a superior anchor, which is coupled to a superior portion of the flexible tether and configured to anchor the flexible tether to a left-atrial site of a wall of a left atrium of a heart; and an inferior anchor, which is coupled to an inferior portion of the flexible tether and configured to anchor the flexible tether to a left-ventricular site of a left ventricle of the heart selected from the group of sites consisting of: (a) a site of a wall of a mid third of the left ventricle, (b) a site of a wall of an apical third of the left ventricle, and (c) a site of a papillary muscle of the left ventricle, wherein the flexible tether is configured such that when the flexible tether is anchored and has a length of 6-12 cm between the superior and the inferior anchors, the flexible tether reduces a volume of the left atrium during at least a portion of ventricular diastole of each cardiac cycle, thereby enhancing ventricular filling.

Inventive Concept 53. The cardiac implant according to Inventive Concept 52, wherein the flexible tether is configured such that when the flexible tether is anchored and has the length of 6-12 cm between the superior and the inferior anchors, the flexible tether reduces the volume of the left atrium by approximating a left atrial roof and a left atrioventricular (AV) plane during the at least a portion of ventricular diastole of each cardiac cycle.

Inventive Concept 54. The cardiac implant according to Inventive Concept 52, wherein the flexible tether is configured such that when the flexible tether is anchored and has the length of 6-12 cm between the superior and the inferior anchors, the flexible tether reduces the volume of the left atrium beginning during a rapid filling phase of diastole of each cardiac cycle.

Inventive Concept 55. The cardiac implant according to Inventive Concept 52, wherein the cardiac implant is configured such that when the flexible tether is anchored and has the length of 6-12 cm between the superior and the inferior anchors, the cardiac implant does not provide a surface having an area of at least 1 cm2 against which leaflets of a mitral valve of the heart coapt during systole of each cardiac cycle.

Inventive Concept 56. The cardiac implant according to Inventive Concept 52, wherein the cardiac implant is configured such that when the flexible tether is anchored and has the length of 6-12 cm between the superior and the inferior anchors, the cardiac implant does not impede motion of leaflets of a mitral valve of the heart during each cardiac cycle.

Inventive Concept 57. The cardiac implant according to Inventive Concept 52, wherein the cardiac implant is configured such that when the flexible tether is anchored and has the length of 6-12 cm between the superior and the inferior anchors, the cardiac implant does not impede regurgitative blood flow through a mitral valve of the heart.

Inventive Concept 58. The cardiac implant according to any one of Inventive Concepts 52-57, wherein the flexible tether is non-extensible.

Inventive Concept 59. The cardiac implant according to any one of Inventive Concepts 52-57, wherein the flexible tether is elastic.

Inventive Concept 60. The cardiac implant according to any one of Inventive Concepts 52-57, wherein the flexible tether is configured such that the length is adjustable after the flexible tether has been anchored.

Inventive Concept 61. The cardiac implant according to Inventive Concept 60, further including a spool disposed along or at either end of the flexible tether, wherein the length is adjustable by rotating the spool.

Inventive Concept 62. The cardiac implant according to any one of Inventive Concepts 52-57, further including a mitral valve clip positioned along the flexible tether such that when the flexible tether is anchored and the mitral valve clip is coupled to two or more leaflets of a mitral valve of the heart, the mitral valve clip coapts the two or more leaflets.

Inventive Concept 63. The cardiac implant according to Inventive Concept 62, wherein the mitral valve clip includes a central passage through which the flexible tether passes.

Inventive Concept 64. The cardiac implant according to any one of Inventive Concepts 52-57, further including a prosthetic mitral valve, which is configured to be implanted at a mitral valve of the heart, and which includes a frame and a centering ring coupled to the frame, wherein the flexible tether passes through the centering ring.

There is additionally provided, in accordance with an Inventive Concept 65 of the present invention, includes cardiac implant for treating diastolic heart failure, the cardiac implant including:

an elongate member;

a superior anchor, which is coupled to a superior portion of the elongate member and configured to anchor the elongate member to a left-atrial site of a wall of a left atrium of a heart; and an inferior anchor, which is coupled to an inferior portion of the elongate member and configured to anchor the elongate member to a left-ventricular site of a left ventricle of the heart selected from the group of sites consisting of: (a) a site of a wall of a mid third of the left ventricle, (b) a site of a wall of an apical third of the left ventricle, and (c) a site of a papillary muscle of the left ventricle, wherein the elongate member is configured such that when the elongate member is anchored and has a length of 6-12 cm between the superior and the inferior anchors:

the elongate member reduces a volume of the left atrium during at least a portion of ventricular diastole of each cardiac cycle, thereby enhancing ventricular filling, and the cardiac implant does not provide a surface having an area of at least 1 cm2 against which leaflets of a mitral valve of the heart coapt during systole of each cardiac cycle.

Inventive Concept 66. The cardiac implant according to Inventive Concept 65, wherein the elongate member includes a rod. The features of the apparatus of Inventive Concept may be implemented in combination with any of the features of Inventive Concepts 53-58 and/or 60, with the rod substituted for the flexible tether.

Inventive Concept 67. The cardiac implant according to Inventive Concept 65, wherein the elongate member includes a flexible tether.

The present invention will be more fully understood from the following detailed description of embodiments thereof, taken together with the drawings, in which:

BRIEF DESCRIPTION OF THE DRAWINGS

FIGS. 1A and 1B are schematic illustrations of a cardiac implant and a method for treating diastolic heart failure, in accordance with an application of the present invention;

DETAILED DESCRIPTION OF APPLICATIONS

Figure 2B:
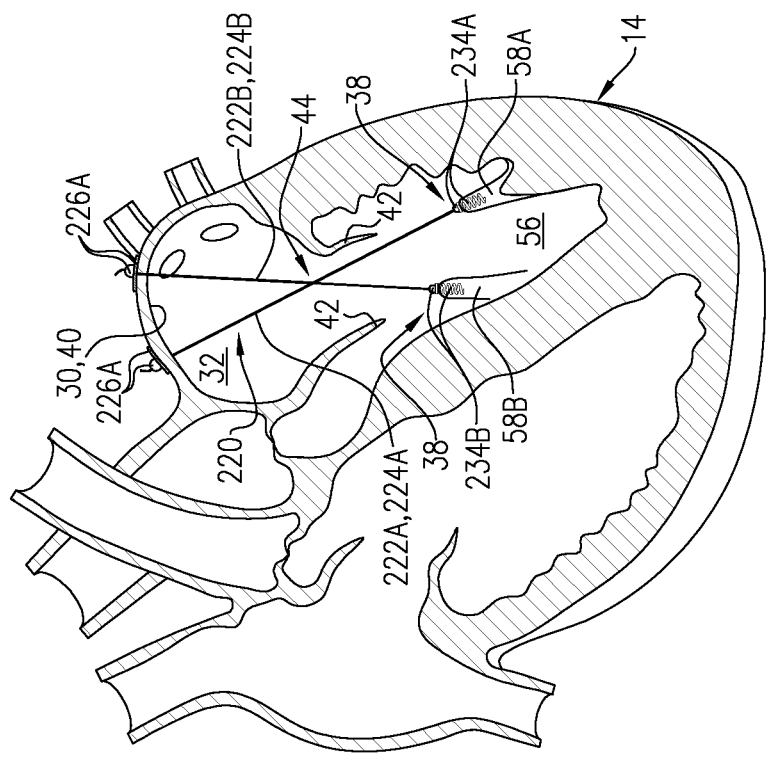
FIG. 2B is a schematic illustration of yet another cardiac implant and a method of treating heart failure, in accordance with an application of the present invention.

FIGS. 1A and 1B are schematic illustrations of a cardiac implant 20 and a method for treating diastolic heart failure, in accordance with an application of the present invention. FIGS. 1A and 1B schematically illustrate a heart 14 during ventricular systole and ventricular diastole, respectively. Cardiac implant 20 is typically implanted in a subject diagnosed as suffering from diastolic heart failure, with or without mitral regurgitation. For some applications, cardiac implant 20 is implanted in a subject diagnosed as suffering from diastolic heart failure without severe mitral regurgitation. For some applications, cardiac implant 20 is implanted in a subject diagnosed as suffering from diastolic heart failure caused at least in part by a loss of atrial kick, which has resulted in a decrease in stroke volume because of decreased left ventricular end-diastolic volume.

Cardiac implant 20 comprises:
an elongate member 22;
a superior anchor 26, which is coupled to a superior portion 28 of elongate member 22 and configured to anchor elongate member 22 to one or more left-atrial sites 46 of one or more walls 30 of a left atrium 32 of heart 14; and
an inferior anchor 34, which is coupled to an inferior portion 36 of elongate member 22 and configured to anchor elongate member 22 to one or more left-ventricular sites 38 of a left ventricle 56 of heart 14.

For example, the one or more walls 30 of left atrium 32 may include one or more of the following:
a left atrial roof 40 (also known in the art as the superior wall), such as shown in FIGS. 1A-B (and FIGS. 2A-B, 3, 4, and 6),
a posterior wall,
a left lateral wall,
a septal (or medial) wall, and/or
an anterior wall.

For example, the one or more left-ventricular sites 38 may include one or more of the following:
a site 38 of a wall 50 of a mid third 52 of left ventricle 56 (mid third 52 is labeled in FIG. 1B, but implantation at this site is not illustrated),
a site 38 of a wall 50 of an apical third 54 of left ventricle 56, such as shown in FIGS. 1A-B (and FIGS. 2A and 3) and labeled in FIG. 1B (apical third 54 includes a ventricular apex 62), and/or
a site 38 of a papillary muscle 58 of left ventricle 56, such as shown in FIG. 2B, described hereinbelow.

For some applications, elongate member 22 comprises a flexible tether 24, such as shown in FIGS. 1A-B (and FIGS. 2A-B, 3, 6, 7A-B, and 8, described hereinbelow). As used in the present application, including the claims, a "flexible tether," unlike a rod, is floppy, i.e., does not have any particular predefined shape between the ends thereof, and does not maintain its shape when not externally constrained to do so. A flexible tether has no or only minimal longitudinal compressive strength (although it typically has high longitudinal tensile strength). A flexible tether does not plastically deform even when curved to a small radius of curvature, e.g., 1 cm.

For example, flexible tether 24 may comprise a polymer, such as a fluoropolymer (e.g., polytetrafluoroethylene (PTFE) or expanded PTFE (ePTFE)), a polyester (e.g., polyethylene terephthalate (PET)), or a polyamide (e.g., nylon); or a metal wire (in which case the metal wire typically has a small diameter, such as a Nitinol or a stainless steel wire, in order to provide the high flexibility described above).

For other applications, elongate member 22 comprises a rod 525, such as described hereinbelow with reference to FIG. 4. For still other applications, elongate member 22 comprises a combination of one or more flexible tethers 24 and one or more rods 525, at different respective longitudinal locations along elongate member 22.

The method illustrated in FIGS. 1A-B comprises implanting cardiac implant 20 by anchoring superior portion 28 of elongate member 22 to the one or more left-atrial sites 46 of the one or more walls of left atrium 32, and anchoring inferior portion 36 of elongate member 22 to the one or more of the left-ventricular sites 38, such that elongate member 22 reduces a volume of left atrium 32 during at least a portion of ventricular diastole of each cardiac cycle, thereby enhancing ventricular filling. The reduction in the volume of left atrium 32 increases pressure in the left atrium and thus the volume of blood flow from the left atrium to the left ventricle. Superior portion 28 may be anchored before or after inferior portion 36 is anchored.

For some applications, elongate member 22 reduces the volume of left atrium 32 by approximating (i.e., moving closer together) left atrial roof 40 and a left atrioventricular (AV) plane 60 during the at least a portion of ventricular diastole of each cardiac cycle. Typically, to do so, during the at least a portion of ventricular diastole, elongate member 22 holds left atrial roof 40 at a fixed distance from ventricular apex 62. As left AV plane 60 and ventricular apex 62 move away from each other during the rapid filling phase of diastole, elongate member 22 prevents left atrial roof 40 and ventricular apex 62 from also moving away from each other. As a result, left atrial roof 40 and left AV plane 60 are approximated. Elongate member 22 thus reduces the volume of left atrium 32 beginning during the rapid filling phase of diastole of each cardiac cycle, thereby enhancing ventricular filling from left atrium 32 during diastole.

The subject treated with the method typically has been diagnosed with diastolic heart failure, with or without mitral regurgitation.

Typically, elongate member 22 is configured such that when elongate member 22 is anchored and has a length of at least 6 cm (e.g., at least 8 cm), no more than 12 cm (e.g., no more than 10 cm), and/or 6-12 cm, such as 6-10 cm, e.g., 8-10 cm, between the one or more left-atrial sites 46 and the one or more left-ventricular sites 38, elongate member 22 reduces the volume of left atrium 32 by approximating left atrial roof 40 and left AV plane 60 during the at least a portion of ventricular diastole of each cardiac cycle. For some applications, elongate member is configured such that when elongate member 22 is anchored and has the above-mentioned length between the one or more left-atrial sites 46 and the one or more left-ventricular sites 38, elongate member 22 reduces the volume of left atrium 32 beginning during a rapid filling phase of diastole of each cardiac cycle.

Typically, superior and inferior portions 28 and 36 of elongate member 22, e.g., flexible tether 24, are anchored such that elongate member 22 does not interfere with leaflets 42 of a mitral valve 44. For example, cardiac implant 20 may be implanted such that cardiac implant 20:

does not provide a surface having an area of at least 1 cm2 against which leaflets 42 of mitral valve 44 coapt during systole of each cardiac cycle, does not impede motion of leaflets 42 of mitral valve 44 during each cardiac cycle, and/or does not impede regurgitative blood flow through mitral valve 44.

Alternatively or additionally, for some applications, cardiac implant 20 is implanted so as to treat the diastolic heart failure without acutely treating mitral regurgitation. Alternatively, the cardiac implant both treats diastolic heart failure and acutely treats mitral regurgitation, such as described hereinbelow with reference to FIG. 6.

For applications in which elongate member 22 comprises rod 525, elongate member is non-extensible, and for some applications in which elongate member 22 comprises flexible tether 24, elongate member 22 is non-extensible. Typically, elongate member 22 has a length of at least 6 cm (e.g., at least 8 cm), no more than 12 cm (e.g., no more than 10 cm), and/or 6-12 cm, such as 6-10 cm, e.g., 8-10 cm, between the one or more left-atrial sites 46 and the one or more left-ventricular sites 38 (although the total length of elongate member 22 may be longer, such as if the elongate member is implanted extending beyond superior anchor 26 and/or inferior anchor 34, and/or elongate member 22 comprises flexible tether 24 and extra length is provided for winding in a spool, such as described hereinbelow with reference to FIG. 3).

For other applications in which elongate member 22 comprises flexible tether 24, flexible tether 24 is elastic, such as slightly elastic.

For still other applications, elongate member 22 comprises a spring at a location along elongate member 22 (configuration not shown). Providing the spring reduces the force applied by the elongate member to the cardiac anchoring sites. The spring may be configured to have a spring constant that results in a desired profile of cardiac tissue movement and blood filling of the left ventricle. The spring may optionally be provided in combination with the slackness provided during ventricular systole, as described immediately below.

Reference is again made to FIGS. 1A-B. For some applications in which elongate member 22 comprises flexible tether 24, superior and inferior portions 28 and 36 of flexible tether 24 are anchored such that flexible tether 24 is:

slack during ventricular systole, such as shown in FIG. 1A, and taut at least during the portion of ventricular diastole during which flexible tether 24 reduces the volume of left atrium 32, such as shown in FIG. 1B.

The slackness of flexible tether 24 during ventricular systole helps prevent any possible interference by the flexible tether with coaptation of leaflets 42 of mitral valve 44 during systole. The tautness of flexible tether 24 during the portion of ventricular diastole does not interfere with mitral valve 44, because leaflets 42 are open during diastole in any event.

The degree of slackness of flexible tether 24 during ventricular systole controls the timing of the commencement of tautness of flexible tether 24 during diastole. If the flexible tether is slacker during systole, the flexible tether becomes taut later in diastole, which delays the point in time during the cardiac cycle at which flexible tether 24 modifies blood flow to the ventricle. (For example, some patients may not need to increase blood flow to the ventricle during early diastole.) The degree of slackness of flexible tether 24 during ventricular systole also controls the maximum approximation of left atrial roof 40 and a left AV plane 60 during the at least a portion of ventricular diastole. If the flexible tether is slacker during systole, the flexible tether causes less approximation of left atrial roof 40 and a left AV plane 60 during diastole, and thus causes less change in blood flow to the ventricle during diastole. Of course, if flexible tether 24 is too slack during systole, the flexible tether will not become taut during diastole and thus will not affect blood flow into the ventricle; therefore, flexible tether 24 is implanted with sufficient tautness to avoid this lack of therapeutic value.

In some applications, a degree of slackness of flexible tether 24 at a certain point during ventricular systole (e.g., at the end of ventricular systole) is selected in order to set a desired time of commencement of tautness of flexible tether 24 during diastole, and/or to set the maximum approximation of left atrial roof 40 and a left AV plane 60 during the at least a portion of ventricular diastole.

Reference is still made to FIGS. 1A-B. For some applications, cardiac implant 20 is implanted using a transcatheter/transvascular approach, a minimally-invasive transapical approach, and/or a combination of transcatheter/transvascular approach and a minimally-invasive transapical approach. For other applications, cardiac implant 20 is implanted in an open-heart procedure.

For some applications, implanting cardiac implant 20 comprises measuring left ventricular end-diastolic volume during one or more cardiac cycles, and setting a length of elongate member 22 between the one or more left-atrial sites 46 and the one or more left-ventricular sites 38 so as to increase the left ventricular end-diastolic volume during one or more subsequent cardiac cycles.

For some applications in which elongate member 22 comprises flexible tether 24, implanting cardiac implant 20 comprises setting a length of flexible tether 24 between the one or more left-atrial sites 46 and the one or more left-ventricular sites 38 such that flexible tether 24 is slack at least at an end of ventricular systole. For some of these applications, setting the length of flexible tether 24 comprises assessing, at the end of ventricular systole of one or more cardiac cycles, a location of left atrial roof 40 with respect to left AV plane 60; and responsively to the location, setting the length of flexible tether 24 between the one or more left-atrial sites 46 and the one or more left-ventricular sites 38 such that flexible tether 24 is slack at least at the end of ventricular systole.

Figure 2A:
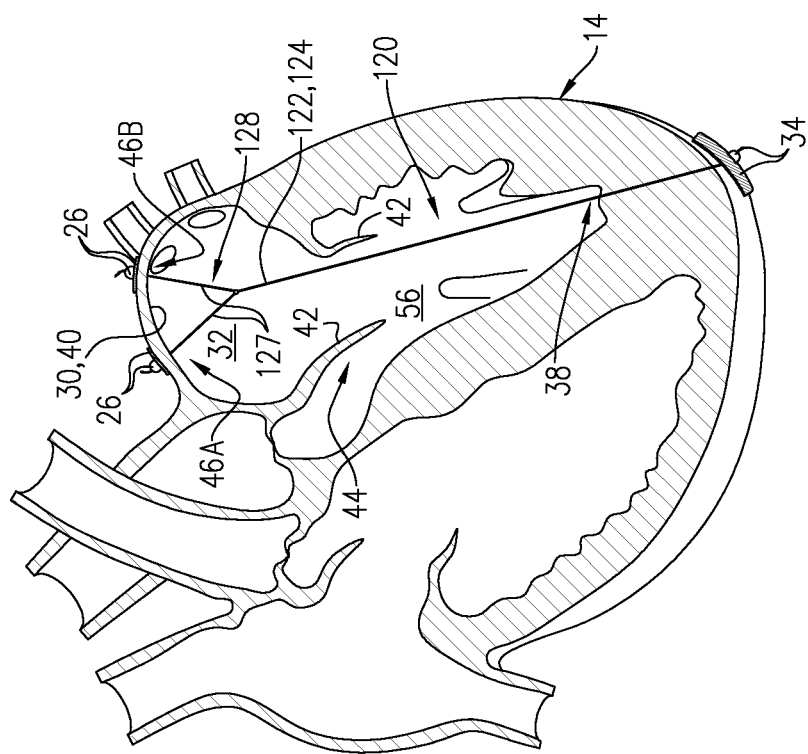
FIG. 2A is a schematic illustration of another cardiac implant and a method of treating heart failure, in accordance with an application of the present invention.

Reference is now made to FIG. 2A, which is a schematic illustration of a cardiac implant 120 and a method of treating heart failure, in accordance with an application of the present invention. FIG. 2A shows heart 14 during ventricular diastole. Other than as described below, cardiac implant 120 is identical to cardiac implant 20, described hereinabove with reference to FIGS. 1A-B, and may implement any of the features thereof, mutatis mutandis.

Cardiac implant 120 comprises an elongate member 122, such as a flexible tether 124. A superior portion 128 of elongate member 122 is shaped so as to define two or more branches 127, e.g., is bifurcated (i.e., has two branches 127). Cardiac implant 120 comprises two or more superior anchors 26, which are coupled to respective branches 127 of superior portion 128 of elongate member 122. Branches (e.g., bifurcations) 127 of superior portion 128 of elongate member 122 are anchored to two respective left-atrial sites 46A and 46B of the one or more left atrial walls 30, such as left atrial roof 40. Providing two or more branches may reduce local stress on left atrial walls 30, and/or cause a broader area of left atrium 32 to be approximated with left AV plane 60.

Reference is now made to FIG. 2B, which is a schematic illustration of a cardiac implant 220 and a method of treating heart failure, in accordance with an application of the present invention. FIG. 2B shows heart 14 during ventricular diastole. Other than as described below, cardiac implant 220 is identical to cardiac implant 20, and may implement any of the features thereof, mutatis mutandis. Alternatively or additionally, the features of cardiac implant 220 may optionally be implemented in combination with the features of cardiac implant 120, described hereinabove with reference to FIG. 2A.

Cardiac implant 220 comprises first and second elongate members 222A and 222B, e.g., first and second flexible tethers 224A and 224B, and corresponding first and second superior anchors 226A and 226B and first and second inferior anchors 234A and 234B. Providing two or more elongate members may reduce local stress on left atrial walls 30, and/or cause a broader area of left atrium 32 to be approximated with left AV plane 60.

For some applications, a first inferior portion 236A and/or a second inferior portion 236 of first and second elongate members 222A and 22B, respectively, is anchored to first and second papillary muscles 58A and 58B, respectively. Alternatively, one or both of first and second inferior portions 236A and 236B are anchored to left-ventricular site 38 of wall of mid third 52 or apical third 54 of left ventricle, such as shown in FIGS. 1A-B and 2A, mutatis mutandis.

Figure 3:
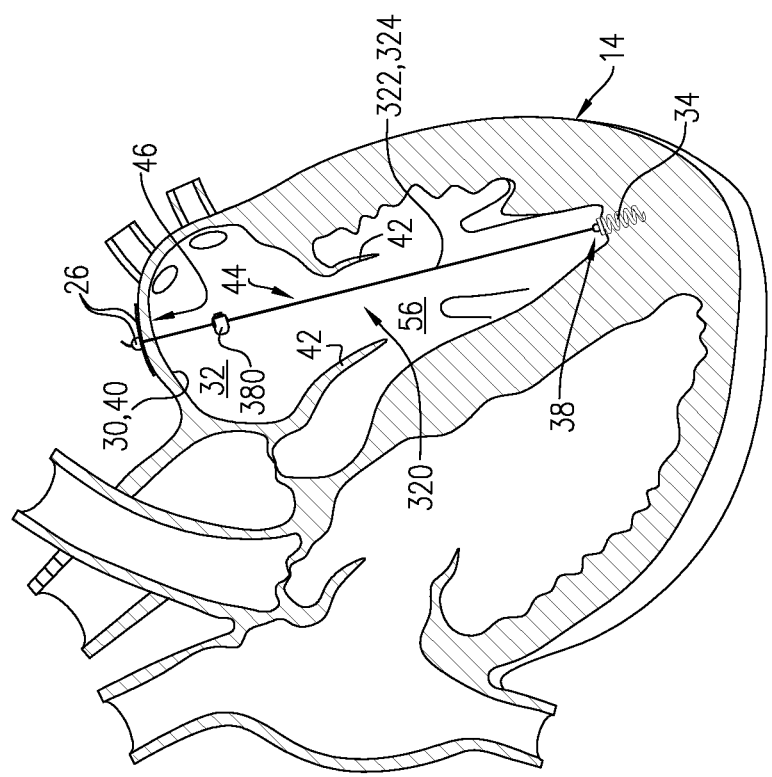
FIG. 3 is a schematic illustration of still another cardiac implant and a method of treating heart failure, in accordance with an application of the present invention.

Reference is now made to FIG. 3, which is a schematic illustration of a cardiac implant 320 and a method of treating heart failure, in accordance with an application of the present invention. FIG. 3 shows heart 14 during ventricular diastole. Other than as described below, cardiac implant 320 is identical to cardiac implant 20, described hereinabove with reference to FIGS. 1A-B, and may implement any of the features thereof, mutatis mutandis. Cardiac implant 320 may also implement any of the features of cardiac implant 120 and/or 220, described hereinabove with reference to FIG. 2A and FIG. 2B, respectively, mutatis mutandis.

Cardiac implant 320 is configured such that a length of an elongate member 322 thereof, e.g., a flexible tether 324, is adjustable after flexible tether 324 has been anchored, such as to provide a length between the one or more left-atrial sites 46 and the one or more left-ventricular sites 38 that is short enough to sufficiently reduce the volume of left atrium 32 during the at least a portion of ventricular diastole, and also long enough to remain slack at least at an end of ventricular systole, so as to maintain left atrial roof 40 at approximately its normal location at the end of ventricular systole and thus avoid reducing atrial volume.

For example, one or more of superior anchor 26 and inferior anchor 34 may provide adjustability to the length of elongate member 322, such as by allowing the elongate member to be drawn through the anchor(s) when the anchor(s) are in an unlocked state, and preventing sliding of the elongate member through the anchor(s) when the anchor(s) are in a locked state (e.g., a crimped state or a reversibly locked state). Alternatively, the elongate member may be shaped so as to define a ratchet that can pass in only one direction through one or more of superior anchor 26 and inferior anchor 34. The adjustability described in this paragraph may be implemented in both configurations in which elongate member 322 comprises flexible tether 324 (as shown) and configurations in which elongate member 322 comprises rod 525, as shown in FIG. 4, mutatis mutandis.

Alternatively or additionally, in some applications in which elongate member 322 comprises flexible tether 324, cardiac implant 320 may comprise a spool 380 disposed along or at either end of the flexible tether. Rotation of the spool adjusts (shortens or lengthens) the effective length of flexible tether 324, by winding a portion of the flexible tether around the spool (to shorten) or unwinding a portion of the flexible tether from the spool (to lengthen). For example, techniques (such as spool assemblies) can be used that are described in one or more of the following patents for adjusting the length of longitudinal members: U.S. Pat. No. 10,517,719 to Miller et al., U.S. Pat. No. 10,751,184 to Reich et al., and/or U.S. Pat. No. 10,610,360 to Reich et al., all of which are incorporated herein by reference.

Further alternatively, an external control, e.g., comprising an energy-transmitting device, can be provided to control tightening and/or loosening of the flexible tether from outside the subject's body. This external control may be implemented in combination with any of the adjustability techniques described above.

For some applications (whether elongate member 322 comprises flexible tether 324 or rod 525), after anchoring superior and inferior portions 28 and 36 of elongate member 322, a length of elongate member 322 between the one or more left-atrial sites 46 and the one or more left-ventricular sites 38 is adjusted, either during an implantation procedure in which the anchoring of superior and inferior portions 28 and 36 of elongate member 322 is performed and/or after completion of the implantation procedure, such as at least 24 hours after anchoring superior and inferior portions 28 and 36 of elongate member 322.

For some applications (whether elongate member 322 comprises flexible tether 324 or rod 525), adjusting the length of elongate member 322 comprises assessing one or more cardiac parameters during one or more pre-adjustment cardiac cycles, and adjusting the length of elongate member 322 responsively to the one or more cardiac parameters. For example, the one or more cardiac parameters may be assessed by performing echocardiography.

For some applications (whether elongate member 322 comprises flexible tether 324 or rod 525), adjusting the length of elongate member 322 comprises measuring left ventricular end-diastolic volume during one or more pre-adjustment cardiac cycles, and adjusting the length of elongate member 322 so as to increase the left ventricular end-diastolic volume during one more post-adjustment cardiac cycles. For some of these applications in which elongate member 322 comprises flexible tether 324, the length of flexible tether 324 is adjusted such that flexible tether 324 is slack at least at an end of ventricular systole, such as described above. For example, adjusting the length of flexible tether 324 may comprise assessing, at the end of ventricular systole of one or more cardiac cycles, a location of left atrial roof 40 with respect to the left AV plane 60; and responsively to the location, adjusting the length of flexible tether 324 such that flexible tether 324 is slack at least at the end of ventricular systole.

Figure 4:
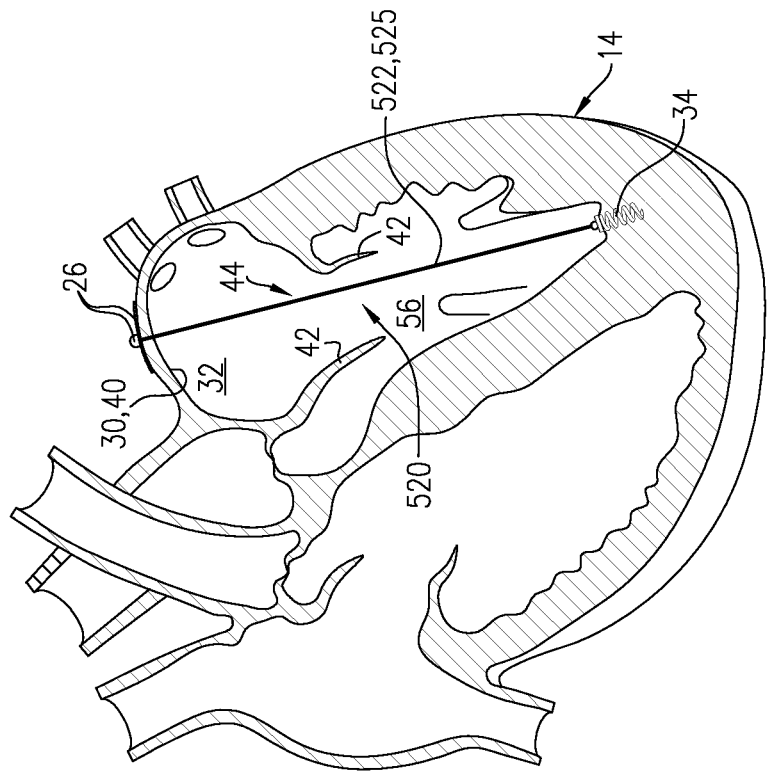
FIG. 4 is a schematic illustration of another cardiac implant, in accordance with an application of the present invention and a method of treating diastolic heart failure, in accordance with an application of the present invention.

Reference is now made to FIG. 4, which is a schematic illustration of a cardiac implant 520, in accordance with an application of the present invention and a method of treating diastolic heart failure, in accordance with an application of the present invention. FIG. 4 shows heart 14 during ventricular diastole. Other than as described below, cardiac implant 520 is identical to cardiac implant 20, described hereinabove with reference to FIGS. 1A-B, and may implement many of the features thereof, mutatis mutandis. Cardiac implant 520 may also implement any of the features of cardiac implant 120 and/or 220, described hereinabove with reference to FIG. 2A and FIG. 2B, respectively, mutatis mutandis.

Cardiac implant 520 comprises an elongate member 522 that comprises a rod 525. Rod 525 is rigid enough to withstand a longitudinal compressive force, and thus is not floppy like flexible tether 24, as described hereinabove.

For example, rod 525 may comprise a metal, such as stainless steel.

Figure 5:
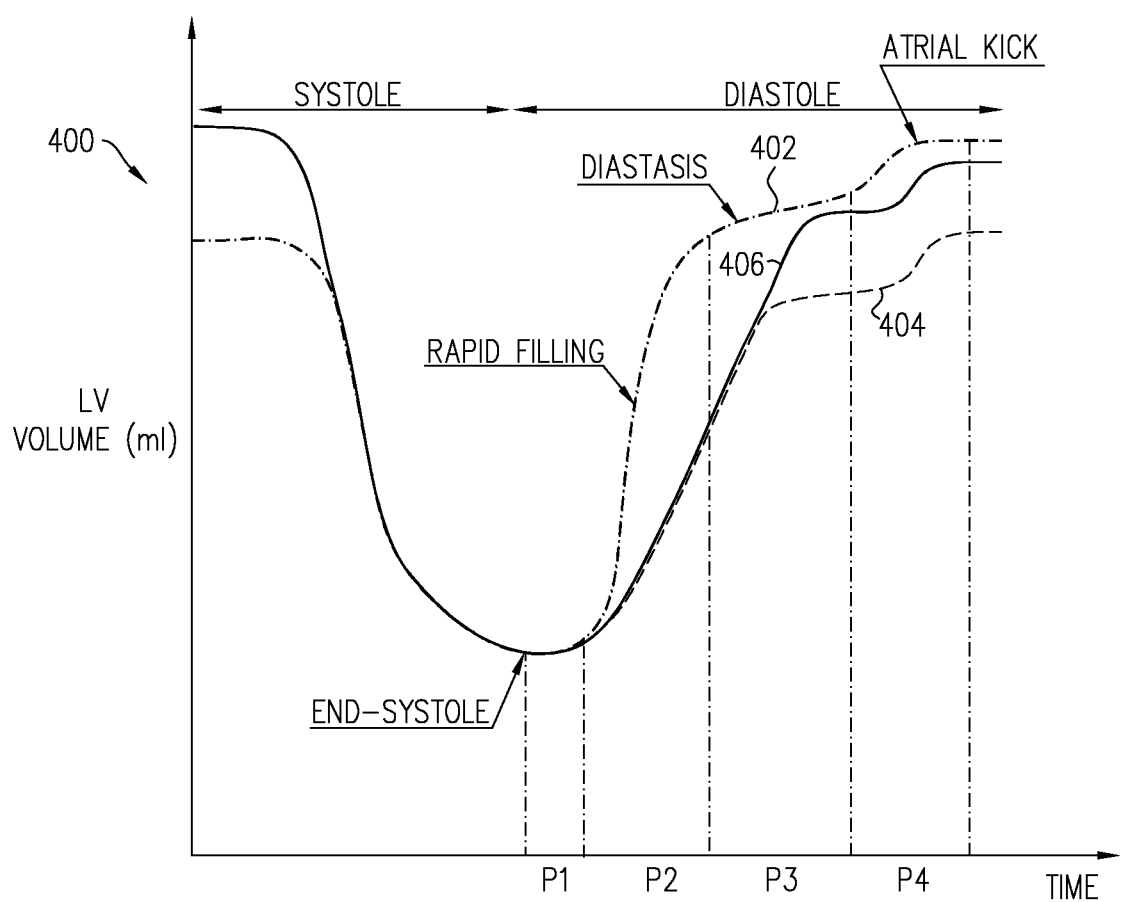
FIG. 5 is a graph including three exemplary left ventricle filling volume curves, two in accordance with the prior art and one in accordance with an application of the present invention.

Reference is now made to FIG. 5, which is a graph 400 including three exemplary left ventricle filling volume curves, two in accordance with the prior art and one in accordance with an application of the present invention. Although graph 400 is described hereinbelow with reference to cardiac implant 20, the graph is equally applicable to the other cardiac implants described herein with reference to FIGS. 1A-8.

As is known in cardiovascular biology, left (LV) ventricle filling during diastole has four phases: (1) an isovolumic relaxation phase (labeled P1 in FIG. 5); (2) a rapid filling phase (labeled P2); (3) diastasis, which is a slow filling phase (labeled P3); and (4) atrial kick, in which final filling occurs during atrial systole (labeled P4).

Graph 400 includes an exemplary normal LV filling volume curve 402, which is typical for a healthy heart not suffering from diastolic heart failure, in accordance with the prior art. The timing of the four phases labeled in graph 400 corresponds to this normal curve.

Graph 400 also includes an exemplary untreated diastolic-heart-failure LV filling volume curve 404, which is typical for a heart suffering from untreated diastolic heart failure, in accordance with the prior art. As can be seen, (a) rapid filling occurs substantially more slowly than in a healthy heart, such that substantially less filling occurs during the rapid filling phase (P2) and continues into the portion of the cardiac cycle that would be diastasis (P3) in a healthy heart (thereby shortening diastasis), (b) diastasis (P3) concludes at a lower filling volume, and (c) diastole concludes with a substantially lower LV end-diastolic volume, characteristic of diastolic heart failure.

Graph 400 further includes a treated diastolic-heart-failure LV filling volume curve 406, which is one exemplary hypothesized effect of treatment using the techniques described herein, in accordance with an application of the present invention. Treated diastolic-heart-failure LV filling volume curve 406 is not based on actual measurements in any human or animal subjects, but instead presents one possible hypothetical result of the treatment described herein. Treatment using the techniques described herein may alternatively result in different pressure curves that also treat diastolic heart failure by increasing ventricular filling during diastole.

As can be seen in the hypothetical exemplary graph, compared to untreated diastolic-heart-failure LV filling volume curve 404, ventricular filling continues for a longer period of time in the portion of the cardiac cycle that would be diastasis (P3) in a healthy heart (thereby shortening diastasis), resulting in a greater filling volume than in the untreated ventricle. Diastasis (P3) thus effectively commences later than in both the healthy heart and the untreated diastolic heart failure heart (P3 is labeled in FIG. 5 based on a healthy heart).

The inventor believes that this extended filling in treated diastolic-heart-failure LV filling volume curve 406 is caused by the increased pressure generated in left atrium 32 by elongate member 22 during a portion of the rapid filling phase (P2), as elongate member 22 approximates left atrial roof 40 and left AV plane 60 during movement of left AV plane 60 away from ventricular apex 62. As a result of this approximation, elongate member 22 reduces the volume of left atrium 32 beginning during the rapid filling phase of diastole, thereby increasing the pressure in the left atrium.

Figure 6:
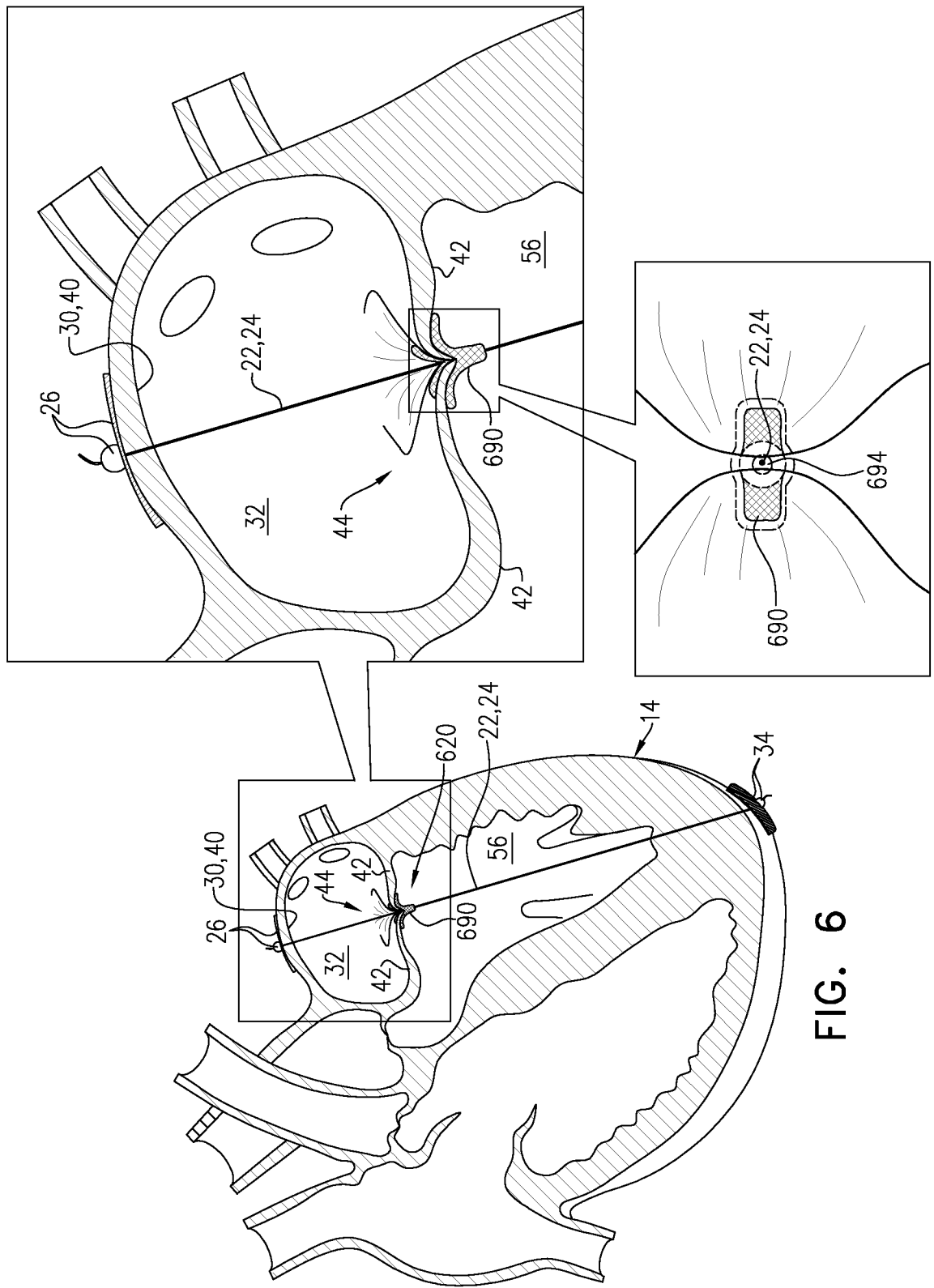
FIG. 6 is a schematic illustration of another cardiac implant and a method of treating diastolic heart failure with mitral regurgitation, in accordance with an application of the present invention.

Reference is now made to FIG. 6, which is a schematic illustration of a cardiac implant 620 and a method of treating diastolic heart failure with mitral regurgitation, in accordance with an application of the present invention. FIG. 6 shows heart 14 during ventricular diastole. Other than as described below, cardiac implant 620 is identical to cardiac implant 20, described hereinabove with reference to FIGS. 1A-B, and may implement any of the features thereof, mutatis mutandis. Cardiac implant 620 may also implement any of the features of cardiac implant 120, 220, and/or 320, described hereinabove with reference to FIG. 2A, FIG. 2B, and FIG. 3, respectively, mutatis mutandis.

Elongate member 22 of cardiac implant 620 typically comprises flexible tether 24. Cardiac implant 620 further comprises a mitral valve clip 690, which is positioned along flexible tether 24, and is configured to be coupled to two or more leaflets 42 of mitral valve 44 such that mitral valve clip 690 coapts the two or more leaflets. Typically, mitral valve clip 690 comprises a central passage 694 through which flexible tether 24 passes.

A method of using cardiac implant 620 comprises positioning mitral valve clip 690 along flexible tether 24 and coupling mitral valve clip 690 to two or more leaflets 42 of mitral valve 44 so as to coapt the two or more leaflets 42 during each cardiac cycle. For some applications, mitral valve clip 690 is positioned along flexible tether 24 such that flexible tether 24 passes through central passage 694 of mitral valve clip 690.

For some applications, mitral valve clip 690 implements some or all of the techniques of:
- the MitraClip™ (Abbott Laboratories, Abbott Park, Ill., USA), e.g., described in U.S. Pat. No. 8,057,493 to Goldfarb et al., which is incorporated herein by reference, or
- the PASCAL Repair System (Edwards Lifesciences, Irvine, Calif., USA), e.g., described in U.S. Pat. No. 11,051,940 to Metchik et al., which is incorporated herein by reference.

Figure 7A:
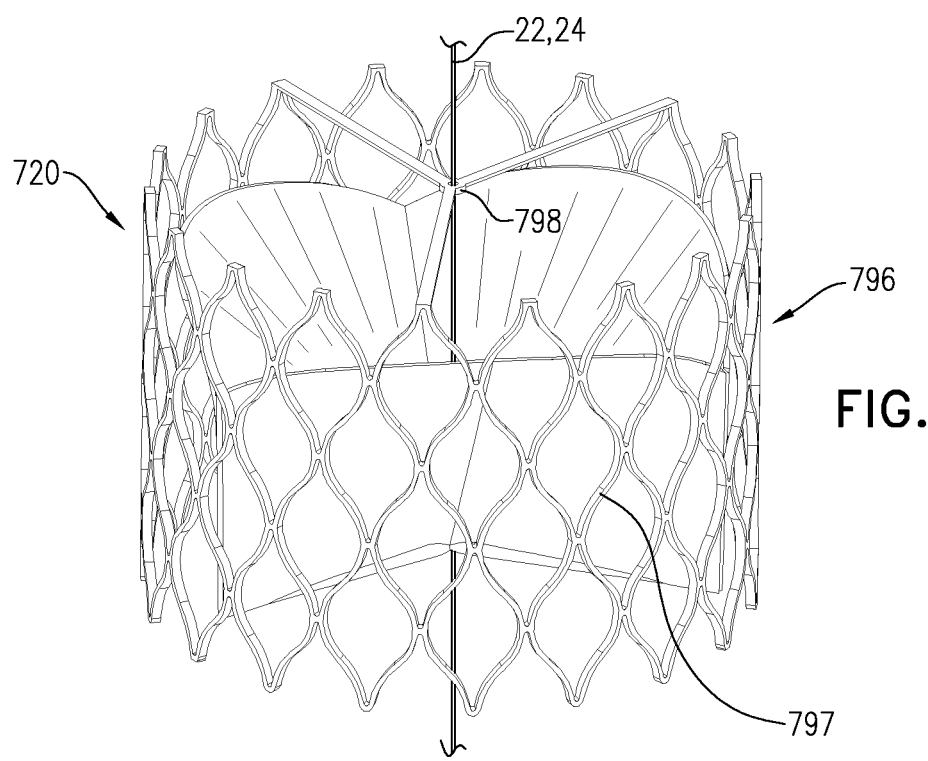
FIGS. 7A-B are schematic illustrations of yet another cardiac implant and a method of treating diastolic heart failure with mitral regurgitation, in accordance with an application of the present invention.
Figure 7B:
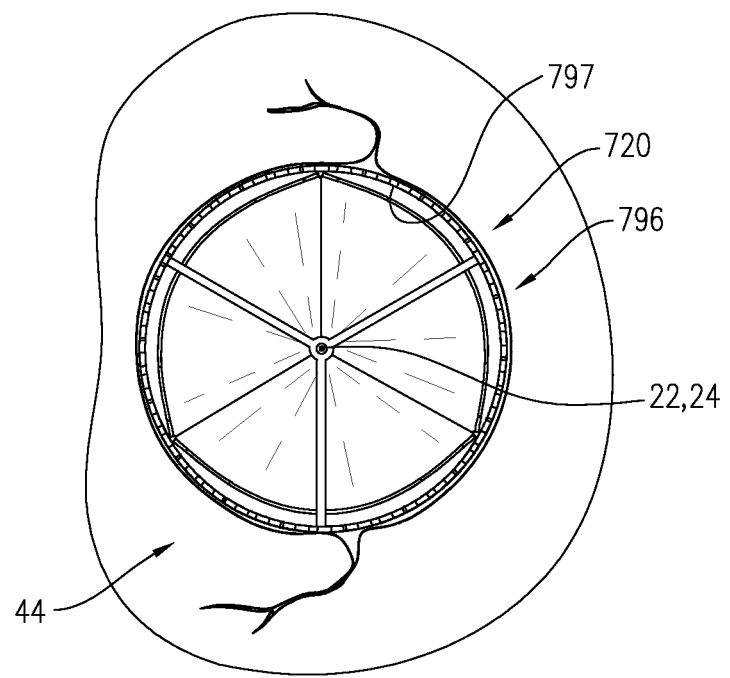

Reference is now made to FIGS. 7A-B, which are schematic illustrations of a cardiac implant 720 and a method of treating diastolic heart failure with mitral regurgitation, in accordance with an application of the present invention. Other than as described below, cardiac implant 720 is identical to cardiac implant 20, described hereinabove with reference to FIGS. 1A-B, and may implement any of the features thereof, mutatis mutandis. Cardiac implant 720 may also implement any of the features of cardiac implant 120, 220, and/or 320, described hereinabove with reference to FIG. 2A, FIG. 2B, and FIG. 3, respectively, mutatis mutandis.

Elongate member 22 of cardiac implant 720 typically comprises flexible tether 24. Cardiac implant 720 further comprises a prosthetic mitral valve 796, which is configured to be implanted at mitral valve 44, and which comprises a frame 797 and a centering ring 798 coupled to the frame, such as by two or more struts of frame 797. Flexible tether 24 passes through centering ring 798. Prosthetic mitral valve 796 may comprise any such prosthesis known in the art, modified as described herein.

A method of using cardiac implant 720 comprises passing flexible tether 24 through centering ring 798 coupled to frame 797 of prosthetic mitral valve 796 implanted at mitral valve 44.

Figure 8:
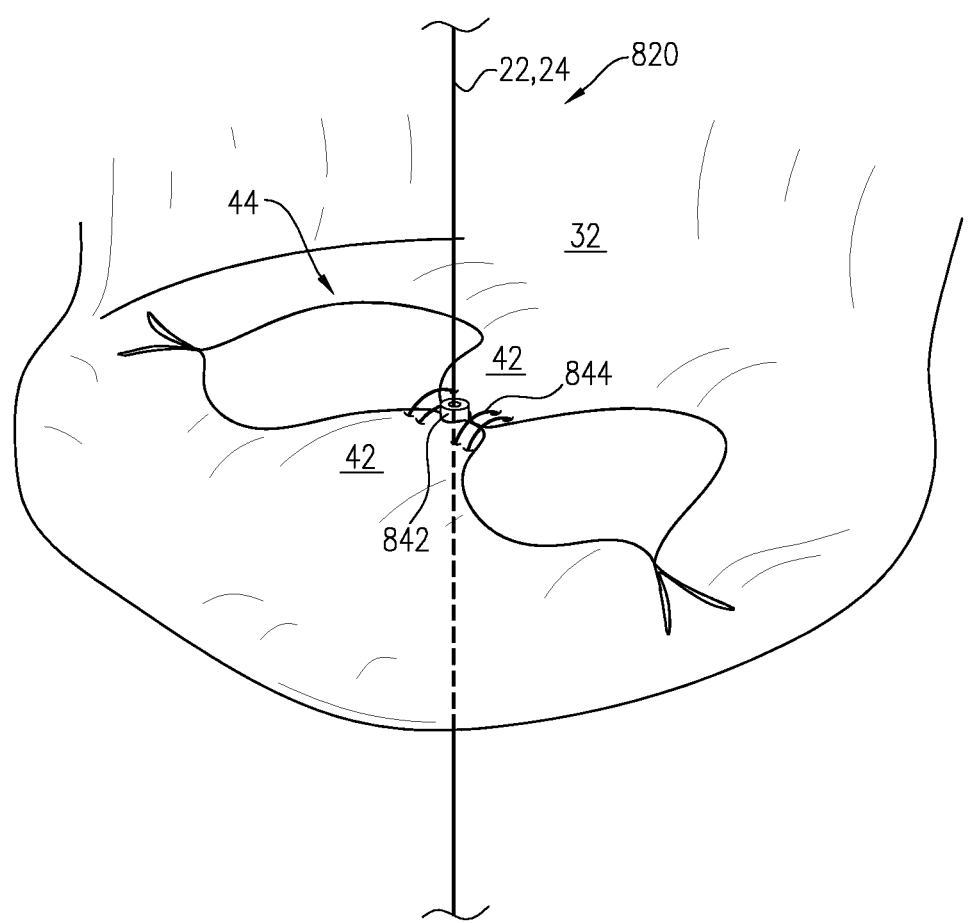
FIG. 8 is a schematic illustration of still another cardiac implant and a method of treating diastolic heart failure with mitral regurgitation, in accordance with an application of the present invention.

Reference is now made to FIG. 8, which is a schematic illustration of a cardiac implant 820 and a method of treating diastolic heart failure with mitral regurgitation, in accordance with an application of the present invention. Other than as described below, cardiac implant 820 is identical to cardiac implant 20, described hereinabove with reference to FIGS. 1A-B, and may implement any of the features thereof, mutatis mutandis. Cardiac implant 820 may also implement any of the features of cardiac implant 120, 220, and/or 320, described hereinabove with reference to FIG. 2A, FIG. 2B, and FIG. 3, respectively, mutatis mutandis.

Elongate member 22 of cardiac implant 820 typically comprises flexible tether 24. Cardiac implant 820 further comprises a ring 842, which is configured to be coupled to mitral valve 44 by an edge-to-edge stitch 844 that approximates free edges of two or more leaflets 42 of mitral valve 44 (also known as an Alfieri stitch). Flexible tether 24 passes through ring 842.

A method is provided comprising passing flexible tether 24 through edge-to-edge stitch 844. Optionally, flexible tether 24 is passed through ring 842, which has been coupled to mitral valve 44 by edge-to-edge stitch 844. Alternatively, flexible tether 24 is passed directly through edge-to-edge stitch 844, in which case ring 842 is not provided.

In case of conflict between definitions provided herein and those provided in the patents incorporated herein by reference, the definitions provided herein will prevail.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of treating diastolic heart failure, comprising implanting a cardiac implant in a heart of a subject diagnosed as suffering from diastolic heart failure, wherein implanting comprises:
    anchoring a superior portion of a flexible tether of the cardiac implant to one or more left-atrial sites of one or more walls of a left atrium of the heart; and
    anchoring an inferior portion of the flexible tether to one or more left-ventricular sites of a left ventricle of the heart selected from the group of sites consisting of: (a) a site of a wall of a mid third of the left ventricle, (b) a site of a wall of an apical third of the left ventricle, and (c) a site of a papillary muscle of the left ventricle, such that the flexible tether reduces a volume of the left atrium during at least a portion of ventricular diastole of each cardiac cycle, thereby enhancing ventricular filling.

2. The method according to claim 1, wherein implanting the cardiac implant in the heart of the subject comprises implanting the cardiac implant in the heart of a subject diagnosed as suffering from diastolic heart failure without mitral regurgitation.

3. The method according to claim 1, wherein implanting the cardiac implant comprises implanting the cardiac implant such that the cardiac implant does not provide a surface having an area of at least 1 cm2 against which leaflets of a mitral valve of the heart coapt during systole of each cardiac cycle.

4. The method according to claim 1, wherein implanting the cardiac implant comprises implanting the cardiac implant such that the cardiac implant does not impede motion of leaflets of a mitral valve of the heart during each cardiac cycle.

5. The method according to claim 1, wherein implanting the cardiac implant comprises implanting the cardiac implant such that the cardiac implant does not impede regurgitative blood flow through a mitral valve of the heart.

6. The method according to claim 1, wherein implanting the cardiac implant comprises implanting the cardiac implant so as to treat the diastolic heart failure without acutely treating mitral regurgitation.

7. The method according to claim 1, wherein implanting the cardiac implant comprises anchoring the superior and the inferior portions of the flexible tether such that the flexible tether reduces the volume of the left atrium by approximating a left atrial roof and a left atrioventricular (AV) plane during the at least a portion of ventricular diastole of each cardiac cycle.

8. The method according to claim 1, wherein implanting the cardiac implant comprises anchoring the superior and the inferior portions of the flexible tether such that the flexible tether reduces the volume of the left atrium beginning during a rapid filling phase of diastole of each cardiac cycle.

9. The method according to claim 1, wherein implanting the cardiac implant comprises anchoring the superior and the inferior portions of the flexible tether such that the flexible tether is slack during ventricular systole and taut at least during the portion of ventricular diastole during which the flexible tether reduces the volume of the left atrium.

10. The method according to claim 1, wherein the flexible tether is non-extensible.

11. The method according to claim 1, wherein implanting the cardiac implant comprises anchoring the superior and the inferior portions of the flexible tether such that the flexible tether has a length of 6-12 cm between the one or more left-atrial sites and the one or more left-ventricular sites.

12. The method according to claim 1, further comprising adjusting a length of the flexible tether between the one or more left-atrial sites and the one or more left-ventricular sites after anchoring the superior and the inferior portions of the flexible tether.

13. The method according to claim 12, wherein adjusting the length of the tether comprises rotating a spool disposed along or at either end of the flexible tether.

14. The method according to claim 12, wherein adjusting the length of the flexible tether comprises:
assessing one or more cardiac parameters during one or more pre-adjustment cardiac cycles; and
adjusting the length of the flexible tether responsively to the one or more cardiac parameters.

15. The method according to claim 12, wherein adjusting the length of the flexible tether comprises:
measuring left ventricular end-diastolic volume during one or more pre-adjustment cardiac cycles; and
adjusting the length of the flexible tether so as to increase the left ventricular end-diastolic volume during one more post-adjustment cardiac cycles.

16. The method according to claim 12, wherein adjusting the length of the flexible tether comprises adjusting the length of the flexible tether such that the flexible tether is slack at least at an end of ventricular systole.

17. The method according to claim 16, wherein adjusting the length of the flexible tether comprises selecting a degree of slackness of the flexible tether in order to set a desired time of commencement of tautness of the flexible tether during diastole of each cardiac cycle.

18. The method according to claim 16, wherein adjusting the length of the flexible tether comprises selecting a degree of slackness of the flexible tether in order to set a desired maximum distance between the left atrial roof and a left atrioventricular plane during the at least a portion of ventricular diastole.

19. The method according to claim 16, wherein adjusting the length of the flexible tether comprises:
assessing, at the end of ventricular systole of one or more cardiac cycles, a location of the left atrial roof with respect to the left AV plane; and
responsively to the location, adjusting the length of the flexible tether such that the flexible tether is slack at least at the end of ventricular systole.

20. The method according to claim 1, wherein implanting the cardiac implant comprises:
measuring left ventricular end-diastolic volume during one or more cardiac cycles; and
setting a length of the flexible tether between the one or more left-atrial sites and the one or more left-ventricular sites so as to increase the left ventricular end-diastolic volume during one or more subsequent cardiac cycles.

21. The method according to claim 1, wherein implanting the cardiac implant comprises setting a length of the flexible tether between the one or more left-atrial sites and the one or more left-ventricular sites such that the flexible tether is slack at least at an end of ventricular systole.

22. The method according to claim 21, wherein setting the length of the flexible tether between the one or more left-atrial sites and the one or more left-ventricular sites comprises selecting a degree of slackness of the flexible tether in order to set a desired time of commencement of tautness of the flexible tether during diastole of each cardiac cycle.

23. The method according to claim 21, wherein setting the length of the flexible tether between the one or more left-atrial sites and the one or more left-ventricular sites comprises selecting a degree of slackness of the flexible tether in order to set a desired maximum distance between the left atrial roof and a left atrioventricular plane during the at least a portion of ventricular diastole.

24. The method according to claim 21, wherein setting the length of the flexible tether comprises: assessing, at the end of ventricular systole of one or more cardiac cycles, a location of the left atrial roof with respect to the left AV plane; and responsively to the location; setting the length of the flexible tether between the one or more left-atrial sites and the one or more left-ventricular sites such that the flexible tether is slack at least at the end of ventricular systole.

25. The method according to claim 1, wherein anchoring the superior portion of the flexible tether to the one or more left-atrial sites of the one or more left atrial walls comprises anchoring the superior portion of the flexible tether to the left atrial roof.

26. The method according to claim 1, wherein the superior portion of the flexible tether is bifurcated, and wherein anchoring the superior portion of the flexible tether to the one or more left-atrial sites of the one or more left atrial walls comprises anchoring bifurcations of the superior portion of the flexible tether to two respective left-atrial sites of the one or more left atrial walls.

27. The method according to claim 1, wherein anchoring the superior portion of the flexible tether comprises anchoring the superior portion of the flexible tether to the one or more left-atrial sites of the one or more walls of the left atrium of the heart of a subject diagnosed as suffering from diastolic heart failure with mitral regurgitation.

28. The method according to claim 27, further comprising positioning a mitral valve clip along the flexible tether and coupling the mitral valve clip to two or more leaflets of a mitral valve of the heart so as to coapt the two or more leaflets.

29. The method according to claim 27, wherein implanting the cardiac implant comprises passing the flexible tether through an edge-to-edge stitch that approximates free edges of two or more leaflets of a mitral valve of the heart.

30. The method according to claim 1, wherein implanting the cardiac implant comprises passing the flexible tether through a centering ring coupled to a frame of a prosthetic mitral valve implanted at a mitral valve of the heart.

31. A method of treating diastolic heart failure, comprising implanting a cardiac implant in a heart of a subject diagnosed as suffering from diastolic heart failure, wherein implanting comprises:
anchoring a superior portion of a rod of the cardiac implant to one or more left-atrial sites of one or more walls of a left atrium of the heart; and
anchoring an inferior portion of the rod to one or more left-ventricular sites of a left ventricle of the heart selected from the group of sites consisting of: (a) a site of a wall of a mid third of the left ventricle, (b) a site of a wall of an apical third of the left ventricle, and (c) a site of a papillary muscle of the left ventricle,
such that the rod reduces a volume of the left atrium during at least a portion of ventricular diastole of each cardiac cycle, thereby enhancing ventricular filling, and
such that the cardiac implant does not provide a surface having an area of at least 1 cm2 against which leaflets of a mitral valve of the heart coapt during systole of each cardiac cycle.

* * * * *